United States Patent
Bewlay et al.

(10) Patent No.: US 10,550,717 B2
(45) Date of Patent: Feb. 4, 2020

(54) THERMAL DEGRADATION MONITORING SYSTEM AND METHOD FOR MONITORING THERMAL DEGRADATION OF EQUIPMENT

(71) Applicant: General Electric Company, Schenectady, NY (US)

(72) Inventors: Bernard Patrick Bewlay, Niskayuna, NY (US); Guanghua Wang, Clifton Park, NY (US); Jason Dees, Ballston Lake, NY (US); William Robb Stewart, Boston, MA (US); Todd Wetzel, Rexford, NY (US)

(73) Assignee: General Electric Company, Schenectady, NY (US)

( * ) Notice: Subject to any disclaimer, the term of this patent is extended or adjusted under 35 U.S.C. 154(b) by 150 days.

(21) Appl. No.: 15/660,290

(22) Filed: Jul. 26, 2017

(65) Prior Publication Data
US 2019/0032507 A1    Jan. 31, 2019

(51) Int. Cl.
| | |
|---|---|
| *G01M 15/14* | (2006.01) |
| *F01D 21/00* | (2006.01) |
| *G05B 23/02* | (2006.01) |
| *G01N 25/72* | (2006.01) |
| *G06T 7/00* | (2017.01) |
| *H04N 5/33* | (2006.01) |

(52) U.S. Cl.
CPC ........... *F01D 21/003* (2013.01); *G01M 15/14* (2013.01); *G01N 25/72* (2013.01); *G05B 23/0291* (2013.01); *G06T 7/0004* (2013.01); *H04N 5/33* (2013.01); *F05D 2220/30* (2013.01); *F05D 2260/80* (2013.01); *G06T 2207/10048* (2013.01); *G06T 2207/30164* (2013.01)

(58) Field of Classification Search
None
See application file for complete search history.

(56) References Cited

U.S. PATENT DOCUMENTS

| | | | |
|---|---|---|---|
| 4,902,139 A | 2/1990 | Adiutori | |
| 6,796,709 B2 | 9/2004 | Choi | |
| 7,021,893 B2 | 4/2006 | Mongillo et al. | |
| 7,690,840 B2 | 4/2010 | Zombo et al. | |

(Continued)

OTHER PUBLICATIONS

MacLeod et al., "Infrared thermal imaging system as a Diagnostic tool for gas turbine engine faults", The American Society of Mechanical Engineers, pp. 1-8, Jun. 13-16, 1994, Hague.

(Continued)

*Primary Examiner* — Pankaj Kumar
*Assistant Examiner* — Charles N Hicks
(74) *Attorney, Agent, or Firm* — Dority & Manning, P.A.

(57) ABSTRACT

Thermal degradation monitoring systems and methods determine at least one operating parameter of equipment that defines prior usage of the equipment, determine at least one thermal characteristic of the equipment using one or more thermal imaging cameras, determine whether both the at least one operating parameter and the at least one thermal characteristic indicate thermal degradation of the equipment, and implement one or more remedial actions on the equipment to change a state of the equipment in response to determining that the at least one operating parameter and the at least one thermal characteristic indicate thermal degradation of the equipment.

22 Claims, 4 Drawing Sheets

(56) References Cited

U.S. PATENT DOCUMENTS

| | | | |
|---|---|---|---|
| 8,505,181 | B1 | 8/2013 | Brostmeyer et al. |
| 9,015,002 | B2 | 4/2015 | Zombo et al. |
| 9,509,923 | B2 | 11/2016 | Pandey et al. |
| 2004/0225482 | A1 | 11/2004 | Vladimirov et al. |
| 2009/0312956 | A1* | 12/2009 | Zombo ............... F01D 5/288 702/34 |
| 2015/0043769 | A1* | 2/2015 | Newman ............... G01N 25/72 382/100 |
| 2016/0140263 | A1 | 5/2016 | Rojas et al. |
| 2018/0118470 | A1* | 5/2018 | Da Silva ............... B65G 15/36 |
| 2018/0154381 | A1 | 6/2018 | Bewlay et al. |

OTHER PUBLICATIONS

Douglas et al., "An integrated approach to the application of high bandwidth optical pyrometry to turbine blade surface temperature mapping", CIASF 99. 18th International Congress on Instrumentation in Aerospace Simulation Facilities. Record (Cat. No. 99CH37025), pp. 4/1-4/6, 1999, Toulouse.

T. Alvarez Tejedor, "Gas turbine materials selection, life management and performance improvement", Power Plant Life Management and Performance Improvement, pp. 330-419, 2011.

Extended European Search Report and Opinion issued in connection with corresponding EP Application No. 18185036.3 dated Dec. 19, 2018.

\* cited by examiner

THERMAL DEGRADATION MONITORING SYSTEM AND METHOD FOR MONITORING THERMAL DEGRADATION OF EQUIPMENT

FIELD

The subject matter described herein relates to monitoring thermal conditions of equipment, such as turbine engines or other equipment, and operating the equipment based on the thermal conditions that are monitored.

BACKGROUND

Thermal performance is a principal element of equipment such as turbine engines (e.g., aircraft engines, industrial gas turbines, etc.). Thermal performance can often degrade during service of the equipment due to component wear, wear of seals in the equipment, cooling circuit degradation, oxidation, corrosion, loss of thermal barrier coatings, and the like. In the case of hot-and-harsh exposure of the equipment, the thermal performance degradation can be particularly severe. A need exists for monitoring thermal performance of equipment to determine how to control (or limit) operations of the equipment, how and/or when to restore thermal performance of the equipment, and/or to determine what operations that the equipment can withstand given the monitored thermal performance.

BRIEF DESCRIPTION

In one embodiment, a method includes determining at least one operating parameter of equipment that defines prior usage of the equipment, determining at least one thermal characteristic of the equipment using one or more thermal imaging cameras, determining whether both the at least one operating parameter and the at least one thermal characteristic indicate thermal degradation of the equipment, and implementing one or more remedial actions on the equipment to change a state of the equipment in response to determining that the at least one operating parameter and the at least one thermal characteristic indicate thermal degradation of the equipment.

In one embodiment, a system includes a thermal remediation controller configured to determine at least one operating parameter of equipment that defines prior usage of the equipment and at least one thermal characteristic of the equipment. The thermal remediation controller also is configured to determine whether both the at least one operating parameter and the at least one thermal characteristic indicate thermal degradation of the equipment. The thermal remediation controller is configured to generate a control signal to direct implementation of one or more remedial actions on the equipment to change a state of the equipment in response to determining that the at least one operating parameter and the at least one thermal characteristic indicate thermal degradation of the equipment.

In one embodiment, a method includes determining at least one operating parameter of equipment that defines prior usage of the equipment. The at least one operating parameter includes one or more of a prior performance characteristic of the equipment or a prior utilization characteristic of the equipment. The method also includes determining at least one thermal characteristic of the equipment using one or more thermal sensors. The at least one thermal characteristic includes one or more of thermal loading of one or more components of the equipment, differential thermal expansion in different regions of the one or more components of the equipment, or a thermal stress in the one or more components of the equipment. The method also includes determining whether both the at least one operating parameter and the at least one thermal characteristic indicate thermal degradation of the equipment, and implementing one or more remedial actions on the equipment to change a state of the equipment in response to determining that the at least one operating parameter and the at least one thermal characteristic indicate thermal degradation of the equipment.

BRIEF DESCRIPTION OF THE DRAWINGS

The present inventive subject matter will be better understood from reading the following description of non-limiting embodiments, with reference to the attached drawings, wherein below.

DETAILED DESCRIPTION

Figure 1:
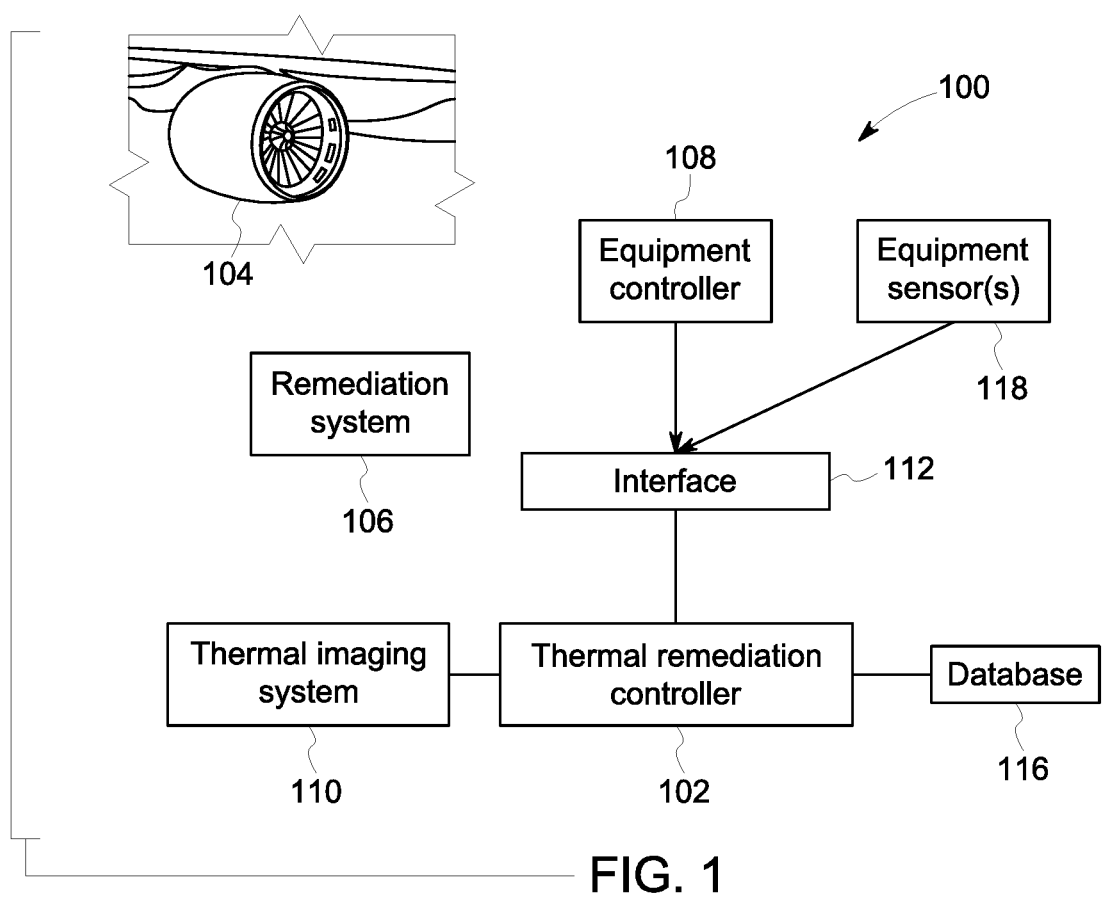
FIG. 1 illustrates one embodiment of an equipment monitoring system.

One or more embodiments of the inventive subject matter described herein provide systems and methods that monitor prior usage and thermal characteristics of equipment, determine thermal degradation of the equipment based on the prior usage and thermal characteristics, and predict a useful life or remaining useful life of the equipment, remediate the thermal degradation, and/or schedule restoration and/or repair of the equipment. While the description herein focuses on engine turbines, the systems and methods can be used with other types of equipment, such as other vehicle components, bridges, rails, or the like. The prediction of the remaining useful service life of equipment can be referred to as lifting the equipment. The predicted remaining useful service life can represent an amount of time that the system or method predict that the equipment can continue to be operational before failing or otherwise being unable to function.

The inventive subject matter described herein provides an analytics-based engine optimizer to improve the thermal performance and life of a turbine engine by assessment of the thermal condition or distress of components in a turbine engine. The thermal distress can be assessed using, for example, a combination of engine operating parameters (as monitored by cumulative exposure on utilization of the engine) together with component thermal information obtained using thermal imaging systems.

The thermal imaging systems can be a thermal imaging camera, or an array of thermal imaging cameras. A single camera can be used to establish thermal maps of the critical thermally loaded regions of components of the equipment. Multiple cameras can be used to establish multi-dimensional thermal maps of the critical thermally loaded regions of components of the equipment. Optionally, the thermal information of the equipment can be obtained by continuous monitoring conventional sensors such as exhaust gas temperature probes, by the insertion of additional instrumentation including optical devices (such as thermal imaging cameras), pyrometers, thermocouples, or the like.

The systems and methods described herein can monitor engine performance and utilization parameters, and correlate these parameters with thermal imaging information obtained during operation of the engine. When thermal degradation is detected, corrective, remedial, or remediation actions can be taken responsive to the thermal degradation reaching identified thresholds. The actions that are implemented can be selected based on the thermal degradation level exceeding predetermined design thresholds, such as low-, medium-, or high-thermal degradation, or when the mean thermal degradation shifts relative to a baseline thermal performance of the equipment. Subsequent maintenance can be predicted and appropriate scheduling can be conducted to reduce or eliminate unplanned outages of the equipment.

With respect to turbine engines of aircraft, the thermal imaging system and installation could include an on-wing configuration for an aircraft engine, or a shop installation for test cell type monitoring. The thermal imaging system and installation could include a field installation for an industrial power turbine. The thermal imaging system can be installed permanently or intermittently, with intermittent use being scheduled at regular intervals or as the result of an unexpected event.

One or more embodiments of inventive subject matter described herein involve communication with components of the gas turbine engines and a remediation system by communication links (e.g., including wired and/or wireless, direct or indirect, connections). The monitoring systems can improve the thermal performance and life of a turbine engine by assessment of the thermal condition or distress level of components in a turbine engine, and by assessment of the use data of the engine. The thermal distress can be caused by or indicative of thermal cycle degradation, such as deterioration of one or more components of equipment caused by or increasing with thermal cycles of the equipment. A thermal cycle of the equipment is use of the equipment that involves heating up of the equipment and/or operating the equipment in elevated temperatures, where the use is repeated one or more times (with each repeated use constituting a thermal cycle).

The monitoring systems can determine or predict when a thermal corrective action or restoration of a turbine engine should be performed. The turbine engine information includes potentially the full flight and full-service exposure data for the turbine engine and the environmental conditions in which the turbine engine has operated. The monitoring systems can predict the efficacy of a selected or recommended thermal restoration procedure. For example, the monitoring system can predict a thermal restoration schedule given a specified objective (e.g., prolong engine life, improve performance, or improve efficiency), based on historical engine data and/or other engine operational data (e.g., the number of thermal cycles of the equipment or engine). The thermal restoration procedures that can be used include, compressor water wash, compressor foam wash, turbine blade external cleaning, turbine blade internal cleaning, thermal barrier restoration, component replacement via a quick turn procedure, and/or de-rating operation of the equipment (e.g., reducing an upper limit or maximum speed at which the equipment or engine is permitted to operate). These procedures can be the corrective, remedial, or remediation actions referred to herein.

The inventive subject matter described herein can extend the life of the equipment without removal of the equipment from an operating location (e.g., without removing a turbine engine from the wing of an aircraft), or in a land based gas turbine installation. Extending the life of the equipment can lead to extended time on wing for an aircraft engine, or extended time between outages for a land based gas turbine. The use of the thermal restoration could also lead to less component damage, and thermal restoration could lead to lower cost repairs.

FIG. 1 illustrates one embodiment of a thermal degradation monitoring system 100. The system 100 includes a thermal remediation controller 102 that monitors one or more operating parameters of equipment 104 and one or more thermal characteristics of the equipment 104. The operating parameters define or otherwise represent prior usage of the equipment 104. The thermal characteristics can be obtained using a thermal imaging system 110, which can represent one or more thermal imaging or infrared cameras. As described herein, the controller 102 examines the operating parameters and the thermal characteristics to determine whether these parameters and characteristics indicate thermal degradation of the equipment 104. The thermal degradation can be locations or regions in the equipment 104 of damage or stress caused at least in part or otherwise resulting from thermal loading of the equipment 104. For example, different regions of the equipment 104 can have different coefficients of thermal expansion and consequently expand or contract different amounts during changes in temperature. The different expansions or contractions can induce stress in the equipment 104, and these stresses can lead to damage in the equipment 104 such as cracks, loss of coatings (e.g., thermal barrier coatings), or the like. Based on the level or amount of thermal degradation, the controller 102 can automatically implement one or more remedial actions on the equipment 104 using a remediation system 106. These actions change a state of the equipment 104, as described herein.

These remedial actions can be performed without removing the equipment 104 from the powered system to which the equipment 104 is coupled, such as the aircraft or wing of the aircraft. The remediation system 106 represents one or more hardware components that change a state of the equipment 104 to reduce the effect of further thermal damage.

Examples of actions that can be implemented by the remediation system 106 to change the state of the equipment 104 include one or more cleaning operations, one or more restoration operations, one or more replacement operations, and/or one or more operative modification operations. The cleaning operations can include applying air, foam, water, or the like, to one or more surfaces or components of the equipment. For example, compressors and/or turbine blades of the equipment 104 can be washed internally and/or externally by applying water and/or a cleaning foam to the compressors and/or turbine blades. Optionally, a filter in the equipment 104 can be cleaned, such as by removing debris or other blockage in the filter that reduces or prevents cooling media (e.g., air or another coolant) from passing through the filter to cool the equipment 104.

The restoration operations can include restoring (e.g., re-applying) a thermal barrier coating onto the equipment 104 or a portion of the equipment 104. The replacement operations can include replacing a part of the equipment 104 (or the entire equipment 104), such as replacing a part of the equipment 104 in a quick-turn procedure, replacing a filter of the equipment 104, or the like.

The operative modification operations can include changes to how the equipment 104 is operated. For example, these operations can include de-rating future or upcoming operation of the equipment 104 by reducing an upper limit or maximum on the speed at which the equipment 104 can operate. Another example includes restricting or placing restrictions on geographic locations or areas where the equipment 104 operates. For example, for equipment 104 exhibiting increased thermal stresses or damage, the remediation system 106 can change a schedule of upcoming travel of a vehicle that includes the equipment 104 to prevent the vehicle and equipment 104 from traveling in locations or areas having elevated temperatures (relative to other locations or areas, or relative to a designated upper temperature limit). For equipment 104 not exhibiting increased thermal stresses or damage (e.g., the thermal stresses or damage in the equipment 104 are less than what is expected or less than one or more other pieces of equipment 104), the remediation system 106 can change a schedule of upcoming travel of a vehicle that includes the equipment 104 so that the vehicle and equipment 104 travels in locations or areas having elevated temperatures (in place of or in addition to other vehicles having equipment 104 with more thermal degradation).

The controllers 102, 108 represent hardware circuitry that includes and/or is connected with one or more processors (e.g., one or more microprocessors, field programmable gate arrays, and/or integrated circuits) that perform the associated operations described herein. Optionally, the controllers 102, 108 can include one or more processors (e.g. a controller, microprocessor, microcontroller, digital signal processor, etc.), one or more memories, one or more input/output subsystems, one or more laptop computers, one or more mobile devices (e.g., a tablet computer, smart phone, body-mounted device or wearable device, etc.), one or more servers, one or more enterprise computer systems, one or more networks of computers, etc. In one embodiment, the equipment controller 108 includes a full authority digital engine controller (FADEC), a component thereof, or as a separate module in communication with the FADEC (e.g., via one or more electronic communication links or networks). In some embodiments, the equipment controller 108 monitors a range of equipment characteristics, such as the frequency of data acquisition and communication with the controller 102.

The controllers 102, 108 can communicate with each other via one or more networks. The network(s) may be, for example, a cellular network, a local area network, a wide area network (e.g., Wi-Fi), a cloud, a virtual personal network (e.g., VPN), a cloud, an Ethernet network, and/or a public network such as the Internet. The controllers 102, 108 can include and/or communicate with each other via communication subsystems. The communication subsystems may enable shorter-range wireless communications between the controllers 102, 108 using, for example, BLUETOOTH and/or other technology. The communication subsystems may include one or more optical, wired and/or wireless network interface subsystems, cards, adapters, or other devices, as may be needed pursuant to the specifications and/or design of the controllers 102, 108.

The thermal imaging system 110 represents one or more thermal imaging cameras, such as infrared cameras. The thermal imaging system 110 optically measures thermal characteristics of the equipment 104, such as temperatures of different regions of the equipment 104. The thermal imaging system 110 can measure the infrared (or other frequency) of radiation emitted or reflected off different surfaces of the equipment 104 as the thermal characteristics. In one embodiment, the thermal imaging system 110 includes multiple cameras that optically sense the thermal characteristics of the same region of the equipment 104 but from different locations, angles, or orientations. These thermal characteristics can be used by the controller 102 to create multi-dimensional thermal maps or images of the thermal characteristics of the equipment 104.

In one embodiment, the thermal imaging system 110 can include or represent one or more non-imaging thermal sensors. These types of sensors can measure temperatures without optically measuring anything about the equipment 104. Examples of these types of sensors include exhaust gas temperature sensors or probes, and thermocouples. These sensors can measure temperatures of the equipment 104 and provide the temperatures to the controller 102 as the thermal characteristics of the equipment 104.

Figure 2:
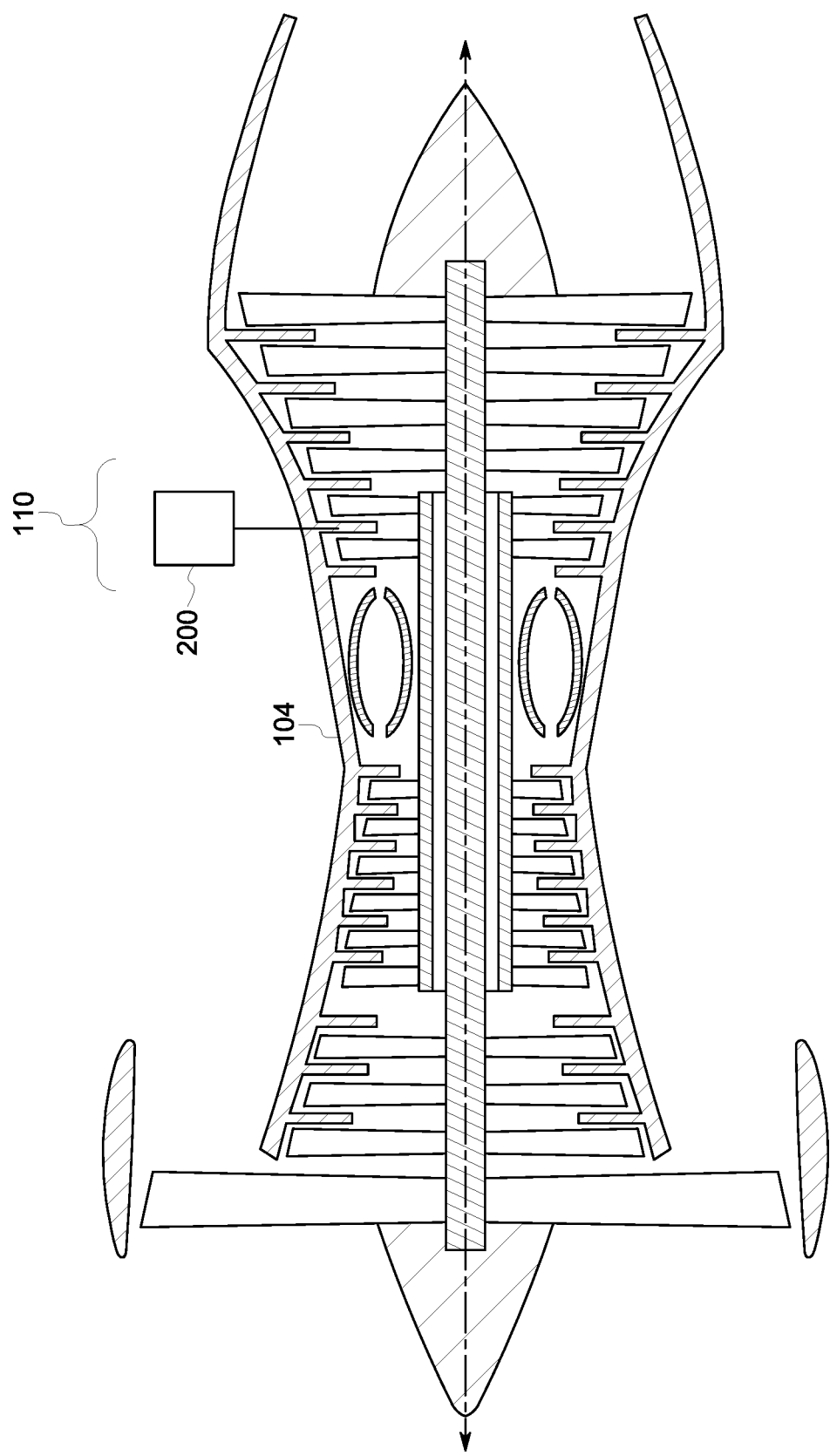
FIG. 2 illustrates one embodiment of a thermal imaging system shown in FIG. 1.
Figure 3:
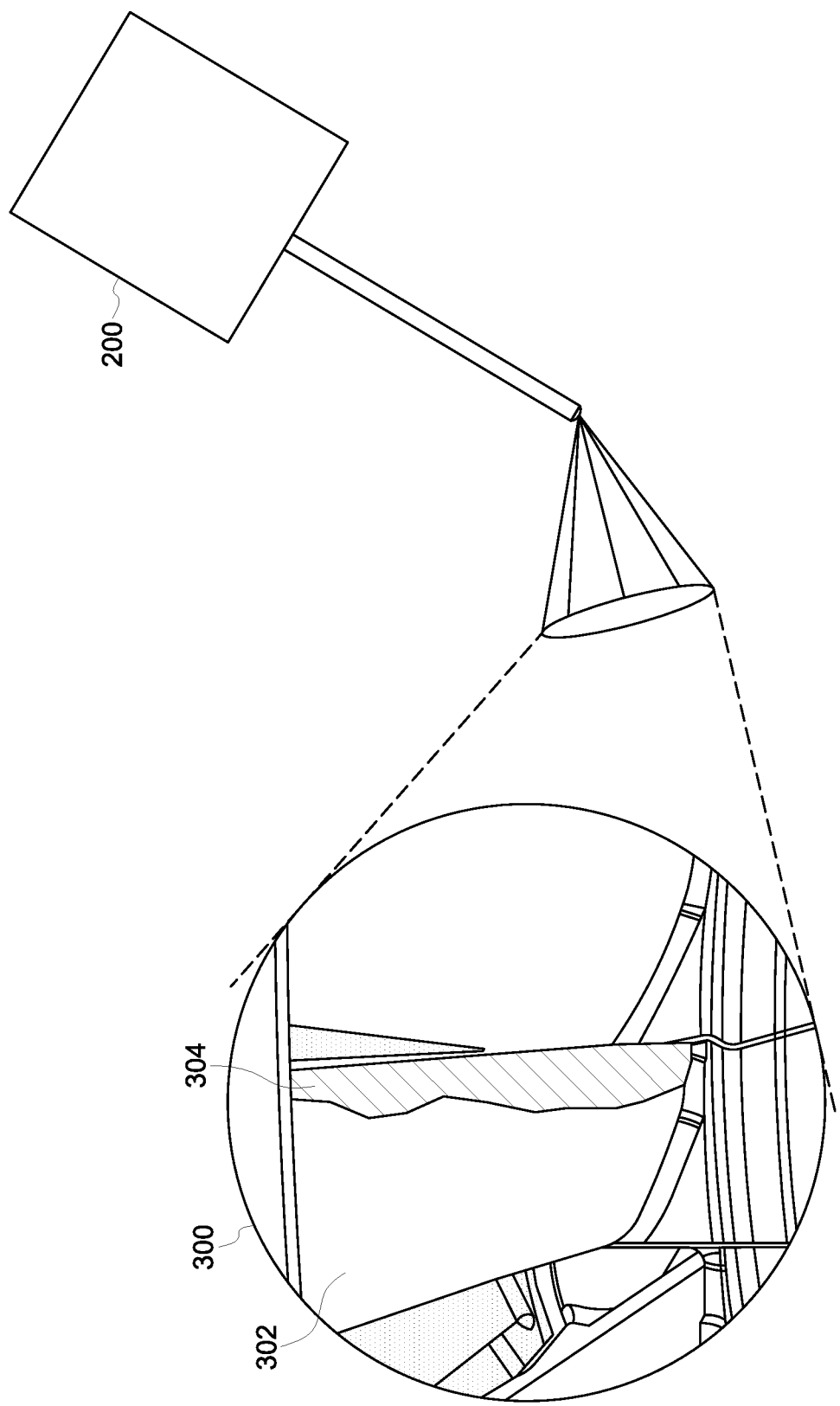
FIG. 3 also illustrates one embodiment of the thermal imaging system shown in FIG. 1.

FIGS. 2 and 3 illustrate one embodiment of the thermal imaging system 110 shown in FIG. 1. The system 110 includes a miniature infrared camera 200 that is at least partially inserted into the equipment 104. The equipment 104 is shown as a turbine engine assembly in FIG. 2. The camera 200 senses infrared radiation (or other radiation) emitted or reflected off surfaces of the equipment 104. Based on the wavelength and intensity of the radiation that is sensed by the camera 200, the camera 200 can generate and/or output a thermal map or image 300 of the sensed radiation. Optionally, the camera 200 can output data signals indicative of the sensed radiation to another component (e.g., the controller 102 shown in FIG. 1), and the other component can create the map or image 300.

In one embodiment, the camera 200 can measure the radiation of the equipment 104 during operation of the equipment 104. For example, the turbine engine can be activated to generate thrust or to operate at an idle setting while the camera 200 senses radiation from the equipment 104. Alternatively, the camera 200 can measure the radiation of the equipment 104 while the equipment 104 is deactivated, such as by measuring the radiation shortly after the equipment 104 is turned off. Optionally, the camera 200 can sense the radiation from the equipment 104 during operation of the equipment 104 and while the equipment 104 is turned off. The measured radiation can indicate temperatures of the equipment 104, and the temperatures (and/or radiation) can be communicated to the controller 102 as thermal characteristics of the equipment 104.

The map or image 300 can represent levels of thermal loading in the equipment 104 using different colors, shapes, styles of lines, etc. For example, different magnitudes of sensed radiation in the equipment 104 can be represented in the map or image 300 using distinct colors. In the example illustrated in FIG. 3, most areas 302 of the equipment 104 are shown in a common color (e.g., red) to indicate that the sensed radiation from these areas 302 was the same or within a designated range of each other (e.g., within 3%). But, a portion of a surface area 304 can be shown in another color (e.g., yellow) to indicate that the magnitude of the sensed radiation from the area 304 is different from the sensed radiation of other surface areas 302 (e.g., outside of the designated range from the radiation of the surfaces 302). The areas 302, 304 in the image 300 having distinct levels of sensed radiation can indicate thermal loading at the interfaces between these areas 302, 304. For example, adjacent (e.g., touching) areas 302, 304 associated with different magnitudes of radiation can indicate that the portions of the equipment 104 that include the areas 302, 304 are at different temperatures. The different temperatures of the areas 302, 304 can mean that the areas 302, 304 are expanding or contracting different amounts. Thermal cycling, temperature gradients, and/or rates of change in the temperatures can impart stress on the equipment 104 in or near (e.g., at boundaries between the areas 302, 304) the areas 302, 304 (e.g., relative to other areas). This increased amount of stress can be an indication of damage to the equipment 104, an indication of a shorter-than-expected useful life of the equipment 104, a need to repair the equipment 104, and/or a need to limit operations of the equipment 104.

The map or image 300 can be a two-dimensional image based on radiation sensed by a single camera 200. Optionally, the map or image 300 can be a three-dimensional image based on radiation sensed by multiple cameras 200. These cameras 200 can be in distinct locations and/or orientations with respect to a common surface of the equipment 104. The different locations and/or orientations can allow for the radiation sensed by the cameras 200 to be combined to generate the three-dimensional image or map. For example, one camera 200 can be positioned and oriented to sense radiation emitted by a first two-dimensional plane inside the equipment 104, which can represent the width and length of a portion of the equipment 104. Another camera 200 can be positioned and oriented to sense radiation emitted by a second two-dimensional plane inside the equipment 104, which can represent the length and height of the portion of the equipment 104. Additional cameras 200 can sense the radiation emitted by other portions of the equipment 104. The radiation sensed by the different cameras 200 can be combined by stitching together or otherwise orienting the two-dimensional data provided by each camera 200 with each other to generate a three-dimensional image or map.

Optionally, the thermal imaging system 110 can include or represent one or more other sensors, such as exhaust gas temperature sensors, pyrometers, and/or thermocouples, that are positioned on or within the equipment 104. These sensors can measure the temperature of different locations on or within the equipment 104. These sensed temperatures can indicate thermal loading of the equipment 104. For example, two locations on or in the equipment 104 that are associated with different sensed temperatures can indicate thermal stress in the equipment 104. The measured temperatures can be communicated to the controller 102 as thermal characteristics of the equipment 104.

Returning to the description of the system 100 shown in FIG. 1, the thermal imaging system 110 can represent or include another source of information on the characteristics of the equipment 104. For example, the sensor 110 can represent an input (e.g., a keyboard, touchscreen, stylus, electronic mouse, antenna, etc.) that is used to provide or receive information on thermal characteristics of the equipment 104, such as an operator that measured the characteristics. This input can be received via an interface 112 (described below). The thermal characteristics of the equipment 104 can be stored in one or more computer readable memories 116, ("Database" in FIG. 1), such as one or more computer hard drives, optical discs, servers, or the like.

The thermal characteristics of the equipment 104 can be provided to the controller 102 by the thermal imaging system 110 as the sensed temperatures and/or radiation described above. The thermal characteristics can be communicated as the measured temperatures or magnitudes of radiation, and/or as the thermal images or maps described above. Optionally, at least one thermal characteristic of the equipment 104 is differential thermal expansion in different regions of one or more components of the equipment 104. The controller 102 can receive the different temperatures from the thermal imaging system 110, and can calculate how much different components of the equipment 104 expand or contract at these temperatures. For example, the controller 102 can store coefficients of thermal expansion of the different types of materials in the equipment 104 in an internal memory, in the database 116, and/or in another location accessible by the controller 102. The controller 102 can calculate how much the different components in the equipment 104 expand or contract based on which materials the components include (e.g., which also can be stored in the internal memory, database 116, and/or another location), the measured temperatures, and the corresponding coefficients of thermal expansion.

Optionally, at least one thermal characteristic of the equipment 104 is thermal stress in one or more components of the equipment 104. The controller 102 can receive the different temperatures from the thermal imaging system 110, and can calculate how much different components of the equipment 104 expands or contracts at these temperatures, as described above. For components that engage or are near each other (e.g., the space or gap between the components is less than how far the components expand due to temperature increases), the controller 102 can calculate or estimate the stress imparted on the components by the thermal expansion. For example, components in the equipment 104 that engage each other and that thermally expand into each other can be calculated or estimated by the controller 102 to have larger thermal stresses imparted on the components than components that do not engage each other or that thermally expand into each other by smaller distances.

The controller 102 also can receive operating parameters of the equipment 104. The operating parameters define or otherwise represent prior usage of the equipment 104. For example, an operating parameter can include a prior performance characteristic of the equipment 104 and/or a prior utilization characteristic of the equipment 104. The prior performance characteristic can indicate how the equipment 104 performed, or generated output, during one or more prior missions, tasks, etc. (e.g., trips) of the equipment 104. Examples of prior performance characteristics of the equipment 104 include previous speeds at which the turbine engine (e.g., the equipment 104) operated, how long the equipment 104 operated at a designated or given speed, and/or a previous setting (e.g., throttle setting) of the equipment 104.

The prior utilization characteristic can indicate how long the equipment 104 operated at or within certain external conditions and/or changes in the condition of the equipment 104. Examples of prior utilization characteristics include a cumulative amount of prior usage of the equipment 104 (e.g., a total amount of time that the equipment 104 has been operating across or among many tasks or missions), a previous servicing of the equipment 104 (e.g., what repairs or maintenance was performed on the equipment 104 and/or when the repairs or maintenance was performed), an environmental condition to which the equipment 104 previously was exposed (e.g., temperatures in which the equipment 104 operated, weather conditions in which the equipment 104 operated, etc.), and/or a change in condition of the equipment 104 between a time before a previously implemented remedial action was performed on the equipment 104 and a time subsequent to the previously implemented remedial action. For example, the change in condition can indicate whether a crack or other damage to the equipment 104 was repaired, whether one or more components of the equipment 104 was replaced, etc. Optionally, the environmental exposure or one or more of the operating parameters can be provided from one or more equipment sensors 118. The equipment sensor 118 can include a thermocouple or other temperature sensitive device that measures operating temperatures of the equipment 104 and/or ambient temperatures.

The interface 112 represents hardware circuitry that includes and/or is connected with one or more communication devices, such as transceiving circuitry, modems, antennas, or the like. The interface 112 receives one or more operating parameters of the equipment 104 from the equipment controller 108. For example, the operating parameters can be communicated via one or more wired and/or wireless connections between the equipment controller 108 and the interface 112. The interface 112 can communicate the operating parameters to the controller 102 and/or the database 116. The controller 102 can obtain the thermal data and/or the operating parameters from the database 116.

The controller 102 receives the operating parameter(s) of the equipment 104 and the thermal characteristic(s) of the equipment 104, examines these parameter(s) and characteristic(s), and determines whether both the operating parameter(s) and the thermal characteristic(s) indicate thermal degradation of the equipment 104. For example, the controller 102 can use empirical correlations, reduced order equations, or other calculations (e.g., finite stress analysis) to predict or determine the thermal stresses that are induced on various components or portions of the equipment 104. As more information is obtained regarding thermal characteristics of the equipment 104, the operational parameters of the same equipment 104, and the consequential reduced useful life of the equipment 104, damage to the equipment 104, need for repair and/or servicing of the equipment 104, etc., the controller 102 can establish correlations between the need for remediation actions and the combination of thermal characteristics and operational parameters of the equipment 104.

For example, larger thermal expansions of neighboring or adjacent components of the equipment 104, hotter operating temperatures of the equipment 104, longer exposure times of the equipment 104 to the elevated operating temperatures, etc., can be associated by the controller 102 with greater thermal stresses or loading on the equipment 104 than smaller thermal expansions of neighboring or adjacent components of the equipment 104, cooler operating temperatures of the equipment 104, shorter exposure times of the equipment 104 to the elevated operating temperatures, etc. The amounts of thermal stress or loading associated with the different combinations of thermal characteristics and operating parameters can be stored in the database 116, and can be based on previous measurements of stress on other equipment 104 having the associated combinations of thermal characteristics and operating parameters.

The controller 102 can determine a residual life of the equipment 104 using the stress analysis referenced above. The residual life optionally can be referred to as a predicted remaining useful service life of the equipment 104, and represents a length of time that the equipment 104 can continue to be used or operate before the thermal loading in the equipment 104 will cause the equipment 104 to fail. The residual life that is determined by the controller 102 can account for the thermal loading or stresses. For example, different stresses can be associated with different designated residual lives in the database 116. The controller 102 can select the residual life from among these designated residual lives as the predicted residual life for the equipment 104 by comparing the stress or stresses determined for the equipment 104, the thermal characteristics measured for the equipment 104, etc., with the stresses and thermal characteristics associated with the different residual lives in the database 116.

The designated residual life having the stress(es) and/or thermal characteristics that match or more closely match the stress(es) and/or thermal characteristics of the equipment 104 (e.g., more closely matches than other designated residual lives) can be selected by the controller 102 as the predicted residual life of the equipment 104.

Optionally, the controller 102 can examine changes in the thermal characteristics and/or operating parameters over time (e.g., trends) to determine whether to implement one or more remedial actions. The controller 102 can trigger a remedial action in response to the thermal characteristics of the equipment being worse than expected given the historical operating parameters of the equipment. For example, different first and second pieces of equipment may operate in the same or substantially similar (e.g., 90% similar) conditions and/or operational settings. The thermal characteristics of these pieces of equipment is expected to be the same or substantially the same. But, the second piece of equipment may present increased thermal damage or stress than the first piece of equipment. The controller 102 can trigger a remedial action to be performed on the second piece of equipment responsive to identifying this increased thermal damage or stress.

With knowledge of the condition of the equipment 104, the controller 102 can implement one or more remedial actions to reduce the effect of operation of the equipment 104. Examples of these remediation actions are described above, and include one or more cleaning operations, one or more restoration operations, one or more replacement operations, and/or one or more operative modification operations.

The controller 102 can generate and communicate one or more signals that trigger a particular procedure to be implemented. For example, the controller 102 can generate and communicate a control signal to the remediation system 106 responsive to the thermal stresses determined by the controller 102 exceeding a first designated threshold and/or the predicted residual life of the equipment 104 falling below a second designated threshold. In one embodiment, the remediation system 106 includes a thermal barrier coating system that enters the equipment 104 (e.g., the combustor) with a 360-degree rail and glider, where the glider has an attachment for a spray tool. The coating system can be one or more of the coating systems described in U.S. patent application Ser. No. 15/460,729, and the tool can be one or more of the spray devices described in U.S. patent application Ser. No. 15/460,729. For example, the coating system can include a rail element and glider element (also referred to herein as a locomotion device) that function to allow 360 degrees of movement in comparison to equipment 104 that needs to be restored or coated. The rail element is an elongated body on which the locomotion device moves along to coat or restore a coating on different locations of the component equipment 104. The rail element may be placed inside the equipment 104 to allow the coating to be applied onto interior surfaces of the equipment 104. An attachment is provided on the locomotion device to receive a spray device, such as an atomizing spray device, to provide the coating (or apply the additive) to the equipment 104. In one embodiment, the coating or additive is utilized to restore a thermal barrier coating of the equipment 104. The spray device receives fluid from one or more reservoirs via one or more pumps to provide a slurry that includes fluid and ceramic particles into the spray device that is atomized and discharged by the spray device to form droplets that impact the equipment 104 to form the coating. The fluid can be water and the ceramic particles can be any solid particles that function to form a coating or that deliver an additive to the equipment 104.

Optionally, the remediation system 106 can represent a scheduling system or dispatch facility that changes a schedule of a vehicle that includes the equipment 104 to prevent the vehicle and equipment 104 from traveling between locations or to a location that would result in the vehicle and equipment 104 moving through elevated temperatures (relative to other locations). As another example, the controller 102 can communicate the control signal to the equipment controller 108 to direct the equipment controller 108 to restrict the operational parameters of the equipment 104. For example, the equipment controller 108 may prevent the throttle of the equipment 104 from being increased above a threshold setting (that is less or lower than the maximum upper throttle of the equipment 104) to reduce the operating temperature of, and thermal stresses in, the equipment 104.

The controller 102 can obtain historical data about the equipment 104 or the history of the remediation actions implemented on the equipment 104, including data obtained during measurements of thermal characteristics of the equipment 104. The controller 102 can use this additional information to determine thermal stresses and/or determine whether to implement one or more remediation actions. For example, the controller 102 can determine that a combination of the thermal characteristics and the operational parameters do not warrant implementing a remediation action. But, the controller 102 can examine historical measurements of the thermal characteristics and determine that the thermal characteristics are increasing at a rapid rate, such as when the differences in temperatures of adjacent or neighboring components of the equipment 104 are increasing by at least a designated rate. Even though the controller 102 may not implement a remedial action due to the recently measured thermal characteristic(s) and/or operational parameters, the controller 102 may determine that the rate of change in the differences in temperatures are sufficiently large that a remedial action is to be implemented.

In one embodiment, the controller 102 can predict when thermal restoration of the equipment 104 should be performed to keep the equipment 104 operational. The thermal restoration can include applying or restoring a coating (e.g., a thermal barrier coating) on the equipment 104. The controller 102 can obtain or receive (e.g., from a schedule of upcoming travel of a vehicle that includes the equipment 104, from operator input, etc.) forthcoming operating parameters of the equipment 104. These parameters can include planned throttle settings, planned horsepower outputs, expected ambient temperatures, and the like, for upcoming operation of the equipment 104. These parameters can be obtained from scheduled operations of the equipment 104, which may dictate the throttle settings, outputs, and/or routes to be traveled by the equipment 104. The ambient conditions (e.g., temperature) can be obtained by reference to weather forecasts for the routes scheduled to be traveled by the equipment 104.

The controller 102 can compare the forthcoming (e.g., expected or planned) operating parameters with designated operating parameters of the equipment 104. The different designated operating parameters can be associated with different thermal stresses or loading of the equipment 104 (e.g., in a memory such as the database 116). The controller 102 can determine which designated operating parameters match or are closer to the forthcoming operating parameters (e.g., closer than one or more other designated operating parameters). The thermal stresses or loading associated with this or these designated operating parameters can be identified by the controller 102 as predicted thermal stress or loading.

Optionally, the controller 102 can compare one or more combinations of forthcoming operating parameters and previously measured thermal characteristics with combinations of designated operating parameters and designated thermal characteristics of the equipment 104. The different combinations of designated operating parameters and thermal characteristics can be associated with different thermal stresses or loading of the equipment 104 (e.g., in a memory such as the database 116). The controller 102 can determine which combination of designated operating parameters and thermal characteristics match or are closer to the combination of forthcoming operating parameters and previously measured thermal characteristics (e.g., closer than one or more other combinations). The thermal stresses or loading associated with the combination of designated operating parameters and thermal characteristics can be identified by the controller 102 as the predicted thermal stress or loading of the equipment 104.

The analysis controller 102 can then inform an operator (e.g., via an output device such as a display, a speaker, or the like) of the predicted thermal stress or loading. The controller 102 optionally can automatically schedule one or more remedial actions to be implemented based on the predicted thermal stress or loading so that the remedial action(s) is implemented before the thermal stress or loading exceeds one or more thresholds.

Figure 4:
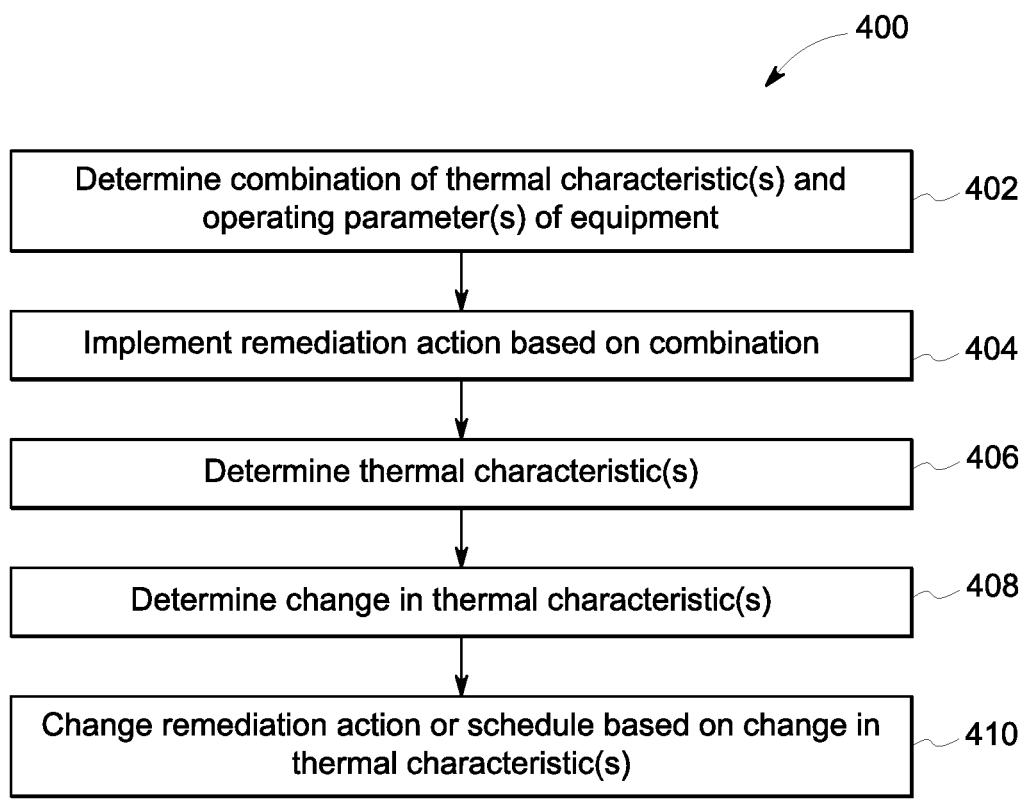
FIG. 4 illustrates a flowchart of one embodiment of a method for monitoring thermal loading in equipment.

FIG. 4 illustrates a flowchart of one embodiment of a method 400 for monitoring thermal degradation in equipment. The method 400 can represent some or all the operations performed by the system 100 described above to monitor thermal loading in the equipment 104, and determine which remediation action(s) to implement to reduce or remove thermal loading in the equipment 104, to implement the remediation action(s), to determine how effective the remediation action was, and/or to change a schedule for upcoming remediation actions.

At 402, one or more combinations of thermal characteristics and operational parameters of the equipment are determined. As described above, these thermal characteristics can be temperatures of the equipment 104 and/or radiation from the equipment 104, and the operational parameters can include throttle settings, engine speeds, and the like. At 304, a remediation action is selected and implemented based on the combination of thermal characteristics and operational parameters. In one embodiment, the remediation action can be selected for implementation responsive to one or more of the thermal characteristics exceeding a designated threshold associated with the operational parameter(s). For example, different thresholds of thermal characteristics can be associated with different designated throttle settings, different operating times, or other operational parameters. These thresholds also can be associated with different remedial actions.

The measured thermal characteristic of the equipment 104 can be compared with the threshold associated with the designated operating parameter that matches or more closely matches the operating parameter of the equipment 104. If the measured thermal characteristic exceeds this threshold, then the remedial action associated with the threshold can be selected.

In one embodiment, the remediation action that is selected can be chosen from among many different remediation actions based on availability information of the different remediation actions. This information can indicate which remediation actions are available at different locations, which personnel that implement the remediation actions are available at different locations, etc. Optionally, the remediation action that is selected can be coordinated with a schedule of the equipment 104. For example, a determination may be made that the equipment 104 needs a remediation action to be performed based on the thermal characteristic(s) and/or the operational parameter(s) of the equipment 104. But, if the equipment 104 is scheduled for other maintenance, the controller 102 may delay implementation of the remediation action until the other maintenance is performed to avoid additional time periods where the equipment 104 is out of service.

At 406, one or more thermal characteristics of the equipment are determined. The thermal characteristics can be determined after implementation of the remediation action. In one embodiment, the same characteristics are determined for the same equipment at 402 and 406. At 408, a change in the thermal characteristics is determined. The thermal characteristics are determined after completion of the remediation action to examine how effective the remediation action was in reducing or eliminating thermal stresses or loading in the equipment 104. For example, the efficacy of the remediation action that was implemented can be quantified by assessing the degree of thermal loading prior to the remediation action via measuring one or more of the thermal characteristics described herein. The degree of thermal loading can be measured again after the remediation action to determine how effective the remediation action was based on how the thermal characteristics changed. If the thermal loading decreased (using the same operational parameters), then the remediation action can be determined to be more effective than another remediation action that resulted in no decrease or a smaller decrease. If the thermal loading increased or did not decrease (e.g., by at least 3%), then the remediation action can be determined to be less effective than another remediation action that resulted in no increase or a smaller increase.

At 410, a remediation action or schedule is changed based on the change in the thermal characteristics. A thermal coating restoration or mitigation schedule can be modified based on the thermal characteristics and/or the effectiveness of different remediation actions. For example, using the determinations of how effective the remediation actions are, the controller 102 can schedule which remediation actions are performed and when the remediation actions are performed to increase residual or remaining useful lives of the equipment 104. Different remediation actions and/or more frequent remediation actions can be scheduled to increase the predicted residual lives of the equipment 104.

Optionally, the remediation schedule can be changed to achieve a specified objective. For example, different remediation schedules can be generated for prolonging the residual life of the equipment, for improving performance of the equipment, for reducing fuel consumption of the equipment, or the like. The schedule that is determined may be determined for an individual piece of equipment, or can be determined for many pieces of equipment (e.g., a fleet-wide schedule). Optionally, the schedule can be modified based on operational parameters of the equipment, such as how often equipment is used, the speeds and/or temperatures at which the equipment operates, etc.

In one embodiment, the remediation schedule is modified based on a remediation cycle time. For example, a determination as to how often remediation actions were needed, how quickly the thermal loading of the equipment progressed between remediation actions, performance of the equipment before and/or after remediation actions, other historical data, etc., can be performed. The remediation actions may need to be performed more or less often based on this historical data in order to improve performance of the equipment without taking the equipment out of service for extended time periods. The controller 102 can determine how often remediation actions are to be performed on a category or type of equipment based on this historical data, and schedule remediation actions for the same type of equipment based on this determination. This frequency at which remediation actions are needed can be used to modify or create the remediation schedule.

One feature of the inventive subject matter described herein includes a method that includes determining at least one operating parameter of equipment that defines prior usage of the equipment, determining at least one thermal characteristic of the equipment using one or more thermal imaging cameras, determining whether both the at least one operating parameter and the at least one thermal characteristic indicate thermal degradation of the equipment, and implementing one or more remedial actions on the equipment to change a state of the equipment in response to determining that the at least one operating parameter and the at least one thermal characteristic indicate thermal degradation of the equipment.

The thermal degradation can be indicated by thermal characteristics that represent hotter components of the equipment than would be expected for the operating parameters. For example, the database 116 can store designated thermal characteristics associated with different operating parameters (e.g., different throttle settings, different durations of operation, or combinations thereof). If the measured thermal characteristics exceed those associated with the operating parameters, then the measured thermal characteristics can indicate thermal degradation, as the equipment appears to be hotter than expected. If the measured thermal characteristics do not exceed those associated with the operating parameters, then the measured thermal characteristics do not indicate thermal degradation, as the equipment is not operating hotter than expected.

The operating parameter can include one or more of a prior performance characteristic of the equipment and/or a prior utilization characteristic of the equipment. The prior performance characteristic can include one or more of a previous engine speed of the equipment, a previous temporal duration of the usage of the equipment, and/or a previous throttle setting of the equipment. The prior utilization characteristic can include one or more of a cumulative amount of prior usage of the equipment, a previous servicing of the equipment, an environmental condition to which the equipment previously was exposed, and/or a change in condition of the equipment between a time before a previously implemented remedial action performed on the equipment and a time subsequent to the previously implemented remedial action.

The thermal characteristic can include one or more of thermal loading of one or more components of the equipment, differential thermal expansion in different regions of the one or more components of the equipment, and/or a thermal stress in the one or more components of the equipment.

The operation of determining whether both the at least one operating parameter and the at least one thermal characteristic indicate the thermal degradation of the equipment can involve determining whether the at least one thermal characteristic is indicative of a different operating parameter than the at least one operating parameter that is determined. For example, if the temperature measured in the equipment is hotter than expected (e.g., than a designated temperature associated with the same throttle setting, duration of use, or combination of throttle setting and duration of use), then the thermal characteristic (i.e., temperature) indicates that the equipment appears to have been operating at a greater throttle setting and/or longer than the actual operation. This can indicate thermal degradation of the equipment as the equipment is operating hotter than expected. For example, the thermal characteristic is indicative of a different operating parameter than the operating parameter of the equipment when the thermal characteristic is associated with more usage of the equipment than is indicated by the operating parameter of the equipment.

The method optionally involves determining a useful life, a remaining useful life, or a combination of the useful life and the remaining useful life of the equipment 104 based on both the at least one operating parameter and the at least one thermal characteristic. For example, if the equipment is operating hotter than expected for an operating parameter of the equipment (e.g., as determined by the controller 102), then the controller 102 can reduce the useful life or determine a shorter useful life of the equipment 104 (e.g., relative to the equipment operating at a temperature that is associated with or cooler than a temperature associated with the operating parameter in the database 116). The one or more remedial actions that can be implemented include the examples of these remediation actions are described above, such as one or more cleaning operations, one or more restoration operations, one or more replacement operations, and/or one or more operative modification operations.

The controller 102 can determine a rate of change in the thermal degradation and modify the schedule of the restoration based on the rate of change. For example, if the controller 102 determines that the thermal loading or thermal stress in the equipment 104 is increasing at a rate that is faster than a designated rate (associated with the operational parameter of the equipment 104 in the database 116), then the controller 102 can create or modify the schedule to have the remediation action performed sooner (relative to the thermal loading or stress increasing at a slower rate). Conversely, if the controller 102 determines that the thermal loading or thermal stress in the equipment 104 is increasing at a rate that is slower than the designated rate, then the controller 102 can create or modify the schedule to have the remediation action performed later to avoid unnecessary maintenance on the equipment 104.

The controller 102 can generate or modify the schedule of the restoration based on an operational objective of the equipment 104. This operational objective can include a limit in one or more of a fuel efficiency of the equipment, audible noise generated by the equipment, and/or emissions generated by the equipment 104. For example, the controller 102 can obtain performance data of the equipment 104, such as the horsepower generated, the fuel consumed, the noise generated, and/or the emissions generated by the equipment 104 at different combinations of thermal characteristics and operational parameters (e.g., throttle settings) of the equipment 104. The controller 102 can determine that the performance data should be improved (e.g., more horsepower generated, less fuel consumed, less noise generated, and/or fewer emissions generated) for the operational parameters, such as from an association (e.g., table, list, etc. in the database 116). The controller 102 can determine that performing remediation will improve the performance data for the same operating parameters, and can schedule the remediation sooner for performance data that needs more improvement than for other performance data. For example, the operational parameter of the equipment 104 can be associated with designated performance data. The measured performance data that is farther from the designated performance data (e.g., relative to other measured performance data) can indicate a need to perform remediation sooner. Conversely, the measured performance data that is closer to the designated performance data (e.g., relative to other measured performance data) can indicate the ability to perform remediation much later.

The schedule of the restoration can be generated or modified for a fleet of equipment that includes the equipment 104 for which the thermal degradation is determined without determining the thermal degradation for all other equipment in the fleet. For example, the controller 102 can determine the thermal degradation for one or more (but not all) pieces of equipment 104 in a fleet for various combinations of operating parameters and measured thermal characteristics. This can involve measuring the thermal degradation for a sample of some, but not all, equipment 104 in the fleet. The controller 102 can determine the thermal degradation of a first set of equipment 104, and can predict that the thermal degradation for the remaining equipment 104 in the fleet as being the same or approximately the same (e.g., within 3%) as the thermal degradation of the first set of equipment 104.

The remediation schedule can be generated or modified by one or more of determining availability of different remedial actions and/or delaying a scheduled instance of the one or more remedial actions based on availability of the equipment 104. The controller 102 can determine at least one forthcoming operating parameter of the equipment 104 and can determine an upcoming amount of change in the thermal degradation in the equipment 104 based on the at least one operating parameter of the equipment 104, the at least one thermal characteristic of the equipment 104, and the at least one forthcoming operating parameter of the equipment 104. The schedule can be generated or modified by the controller 102 also based on the upcoming amount of change in the thermal degradation that is determined. For example, the controller 102 can determine (e.g., predict) forthcoming operational parameters of the equipment 104 and can predict a change in thermal degradation of the equipment 104. This change can be predicted based on previously measured changes in thermal degradation of the equipment 104 when the equipment 104 operated using the same or similar operational parameters as the forthcoming operational parameters.

Optionally, the schedule can be modified by selecting or delaying a remediation action based on a current maintenance schedule of the equipment 104. For example, the equipment 104 may be in need of one or more remediation actions based on the thermal degradation that is identified. The possible remediation actions to be implemented can be a first, expensive and/or time-consuming action (e.g., taking the equipment 104 off-line for replacement of one or more parts of the equipment 104) or a second, less expensive and/or less time-consuming action (e.g., washing the equipment 104). The first remediation action can be associated with a longer extension of the useful life of the equipment 104 when compared with the second remediation action. But, if the second remediation action will extend the useful life of the equipment 104 until at least the next scheduled maintenance event (e.g., a regularly scheduled maintenance), while the first remediation action will extend the useful life of the equipment 104 much longer, then the controller 102 can select the second remediation action for implementation. The different remediation actions can be associated with previously defined or designated extensions of useful lives of the equipment 104. This information can be stored in one or more databases 116 and be accessed by the controller 102 to determine which action to implement.

In one embodiment, a method includes determining at least one operating parameter of equipment that defines prior usage of the equipment, determining at least one thermal characteristic of the equipment using one or more thermal imaging cameras, determining whether both the at least one operating parameter and the at least one thermal characteristic indicate thermal degradation of the equipment, and implementing one or more remedial actions on the equipment to change a state of the equipment in response to determining that the at least one operating parameter and the at least one thermal characteristic indicate thermal degradation of the equipment.

Optionally, the method also can include determining one or more additional thermal characteristics of the equipment subsequent to implementing the one or more remedial actions on the equipment, determining a change from the at least one thermal characteristic determined prior to implementation of the one or more remedial actions on the equipment to the one or more additional thermal characteristics of the equipment subsequent to implementing the one or more remedial actions on the equipment, and changing which of one or more additional remedial actions is scheduled to be implemented on the equipment and/or changing when the one or more additional remedial actions is scheduled to be implemented on the equipment based on the change that is determined.

Optionally, the at least one operating parameter includes one or more of a prior performance characteristic of the equipment or a prior utilization characteristic of the equipment.

Optionally, the prior performance characteristic includes one or more of a previous speed of the equipment, a previous temporal duration of the usage of the equipment, or a previous throttle setting of the equipment.

Optionally, the prior utilization characteristic includes one or more of a cumulative amount of prior usage of the equipment, a previous servicing of the equipment, an environmental condition to which the equipment previously was exposed, or a change in condition of the equipment between a time before a previously implemented remedial action performed on the equipment and a time subsequent to the previously implemented remedial action.

Optionally, the equipment is a turbine engine.

Optionally, the at least one thermal characteristic includes one or more of thermal loading of one or more components of the equipment, differential thermal expansion in different regions of the one or more components of the equipment, a thermal stress in the one or more components of the equipment, or a condition of a surface or coating in the equipment due to thermal loading or thermal cycles of the equipment.

Optionally, determining whether both the at least one operating parameter and the at least one thermal characteristic indicate the thermal degradation of the equipment involves determining whether the at least one thermal characteristic indicates greater thermal degradation in the equipment than is associated with the at least one operating parameter.

Optionally, the at least one thermal characteristic is indicative of the different operating parameter when the at least one thermal characteristic is associated with more usage of the equipment than is indicated by the at least one operating parameter.

Optionally, the method also includes determining a useful life, a remaining useful life, or a combination of the useful life and the remaining useful life of the equipment based on both the at least one operating parameter and the at least one thermal characteristic.

Optionally, the one or more remedial actions that are implemented includes one or more of a cleaning operation of the equipment, a restoration operation of the equipment, a replacement operation of the equipment, or an operative modification operation of the equipment.

Optionally, the method also includes determining when an upcoming maintenance event to be performed on the equipment is already scheduled, and selecting a first remedial action of the one or more remedial actions to implement based on which of the one or more remedial actions will extend a useful life of the equipment to at least the upcoming maintenance event while not selecting a different, second remedial action of the one or more remedial actions that will extend the useful life of the equipment longer than the first remedial action.

Optionally, the at least one thermal characteristic is determined from a sample of the equipment in a larger fleet of the equipment without determining the at least one thermal characteristic for all the equipment in the fleet. The method also can include implementing the one or more remedial actions on the equipment in the fleet that is outside of the sample to change the state of the equipment in the fleet that is outside of the sample based on the at least one thermal characteristic that is determined for the sample.

In one embodiment, a system includes a thermal remediation controller configured to determine at least one operating parameter of equipment that defines prior usage of the equipment and at least one thermal characteristic of the equipment. The thermal remediation controller also is configured to determine whether both the at least one operating parameter and the at least one thermal characteristic indicate thermal degradation of the equipment. The thermal remediation controller is configured to generate a control signal to direct implementation of one or more remedial actions on the equipment to change a state of the equipment in response to determining that the at least one operating parameter and the at least one thermal characteristic indicate thermal degradation of the equipment.

Optionally, the thermal remediation controller is configured to obtain the at least one thermal characteristic from one or more thermal imaging cameras.

Optionally, the at least one operating parameter includes one or more of a prior performance characteristic of the equipment or a prior utilization characteristic of the equipment.

Optionally, the at least one thermal characteristic includes one or more of thermal loading of one or more components of the equipment, differential thermal expansion in different regions of the one or more components of the equipment, or a thermal stress in the one or more components of the equipment.

Optionally, the thermal remediation controller is configured to determine whether both the at least one operating parameter and the at least one thermal characteristic indicate the thermal degradation of the equipment by determining whether the at least one thermal characteristic is indicative of a different operating parameter than the at least one operating parameter that is determined.

Optionally, the thermal remediation controller also is configured to determine a useful life, a remaining useful life, or a combination of the useful life and the remaining useful life of the equipment based on both the at least one operating parameter and the at least one thermal characteristic.

In one embodiment, a method includes determining at least one operating parameter of equipment that defines prior usage of the equipment. The at least one operating parameter includes one or more of a prior performance characteristic of the equipment or a prior utilization characteristic of the equipment. The method also includes determining at least one thermal characteristic of the equipment using one or more thermal sensors. The at least one thermal characteristic includes one or more of thermal loading of one or more components of the equipment, differential thermal expansion in different regions of the one or more components of the equipment, or a thermal stress in the one or more components of the equipment. The method also includes determining whether both the at least one operating parameter and the at least one thermal characteristic indicate thermal degradation of the equipment, and implementing one or more remedial actions on the equipment to change a state of the equipment in response to determining that the at least one operating parameter and the at least one thermal characteristic indicate thermal degradation of the equipment.

Optionally, determining whether both the at least one operating parameter and the at least one thermal characteristic indicate the thermal degradation of the equipment involves determining whether the at least one thermal characteristic is indicative of a different operating parameter than the at least one operating parameter that is determined. The at least one thermal characteristic can be indicative of the different operating parameter when the at least one thermal characteristic is associated with more usage of the equipment than is indicated by the at least one operating parameter.

Optionally, the method also includes determining a useful life, a remaining useful life, or a combination of the useful life and the remaining useful life of the equipment based on both the at least one operating parameter and the at least one thermal characteristic.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   determining, by a controller, at least one operating parameter of equipment that defines prior usage of the equipment;
   receiving, by the controller, an input indicative of a temperature or a magnitude of radiation of one or more components of the equipment;
   determining, by the controller, at least one thermal characteristic of the equipment based at least in part on the input, wherein the at least one thermal characteristic includes differential thermal expansion in different regions of the one or more components of the equipment;
   determining, by the controller, whether both the at least one operating parameter and the at least one thermal characteristic indicate thermal degradation of the equipment; and
   implementing, by a remediation system, one or more remedial actions on the equipment to change a state of the equipment in response to the controller determining that the at least one operating parameter and the at least one thermal characteristic indicate thermal degradation of the equipment.

2. The method of claim 1, further comprising:
   determining one or more additional thermal characteristics of the equipment subsequent to implementing the one or more remedial actions on the equipment;
   determining, by the controller, a change from the at least one thermal characteristic determined prior to implementation of the one or more remedial actions on the equipment to the one or more additional thermal characteristics of the equipment subsequent to implementing the one or more remedial actions on the equipment; and
   changing which of one or more additional remedial actions is scheduled to be implemented on the equipment, changing when the one or more additional remedial actions is scheduled to be implemented on the equipment, or changing both which of the one or more additional remedial actions is scheduled and when the one or more additional remedial actions is scheduled based on the change that is determined by the controller.

3. The method of claim 1, wherein the at least one operating parameter includes one or more of a prior performance characteristic of the equipment or a prior utilization characteristic of the equipment.

4. The method of claim 3, wherein the prior performance characteristic includes one or more of a previous speed of the equipment, a previous temporal duration of the usage of the equipment, or a previous throttle setting of the equipment.

5. The method of claim 3, wherein the prior utilization characteristic includes one or more of a cumulative amount of prior usage of the equipment, a previous servicing of the equipment, an environmental condition to which the equipment previously was exposed, or a change in condition of the equipment between a time before a previously implemented remedial action performed on the equipment and a time subsequent to the previously implemented remedial action.

6. The method of claim 1, wherein the equipment is a turbine engine.

7. The method of claim 1, wherein determining, by the controller, the at least one thermal characteristic of the equipment based at least in part on the input comprises:
  accessing, by the controller, coefficients of thermal expansion corresponding to materials of the one or more components of the equipment;
  correlating the temperature or the magnitude of radiation of the one or more components of the equipment received as part of the input with the accessed coefficients of thermal expansion corresponding to materials of the one or more components of the equipment; and
  calculating the differential thermal expansion in different regions of the one or more components of the equipment based at least in part on correlating the temperature or the magnitude of radiation of the one or more components of the equipment received as part of the input with the accessed coefficients of thermal expansion corresponding to materials of the one or more components of the equipment.

8. The method of claim 1, wherein determining, by the controller, whether both the at least one operating parameter and the at least one thermal characteristic indicate the thermal degradation of the equipment involves determining, by the controller, whether the at least one thermal characteristic indicates greater thermal degradation in the equipment than is associated with the at least one operating parameter wherein the at least one operating parameter is indicative of a throttle setting of the equipment.

9. The method of claim 8, wherein the at least one thermal characteristic is indicative of the different operating parameter when the at least one thermal characteristic is associated with more usage of the equipment than is indicated by the at least one operating parameter.

10. The method of claim 1, further comprising determining, by the controller, a useful life, a remaining useful life, or a combination of the useful life and the remaining useful life of the equipment based on both the at least one operating parameter and the at least one thermal characteristic.

11. The method of claim 1, wherein the one or more remedial actions that are implemented includes an operative modification operation of the equipment, wherein the operative modification operation of the equipment includes reducing an upper limit at which the equipment can operate.

12. The method of claim 1, further comprising:
  determining, by the controller, when an upcoming maintenance event to be performed on the equipment is scheduled; and
  selecting, by the controller, a first remedial action of the one or more remedial actions to implement based on which of the one or more remedial actions will extend a useful life of the equipment to at least the upcoming maintenance event while not selecting a different, second remedial action of the one or more remedial actions that will extend the useful life of the equipment longer than the first remedial action.

13. The method of claim 1, wherein the at least one thermal characteristic is determined from a sample of the equipment in a larger fleet of the equipment without determining the at least one thermal characteristic for all the equipment in the fleet, and further comprising implementing the one or more remedial actions on the equipment in the fleet that is outside of the sample to change the state of the equipment in the fleet that is outside of the sample based on the at least one thermal characteristic that is determined for the sample.

14. A system comprising:
  a thermal remediation controller configured to determine at least one operating parameter of a turbine engine, the at least one operating parameter defines prior usage of the turbine engine and at least one thermal characteristic of the turbine engine, the thermal remediation controller also configured to determine whether both the at least one operating parameter and the at least one thermal characteristic indicate thermal degradation of the turbine engine, wherein the at least one thermal characteristic includes at least one of differential thermal expansion in different regions of one or more components of the turbine engine and a thermal stress in at least one of a first component and a second component operable to engage one another during operation of the turbine engine due to thermal expansion;
  wherein the thermal remediation controller is configured to generate a control signal to direct implementation of one or more remedial actions on the turbine engine to change a state of the turbine engine in response to determining that the at least one operating parameter and the at least one thermal characteristic indicate thermal degradation of the turbine engine.

15. The system of claim 14, wherein the thermal remediation controller is configured to obtain the at least one thermal characteristic from one or more thermal imaging cameras.

16. The system of claim 14, wherein the at least one operating parameter includes one or more of a prior performance characteristic of the turbine engine or a prior utilization characteristic of the turbine engine.

17. The system of claim 14, wherein the at least one thermal characteristic further includes thermal loading of one or more components of the turbine engine.

18. The system of claim 14, wherein the thermal remediation controller is configured to determine whether both the at least one operating parameter and the at least one thermal characteristic indicate the thermal degradation of the turbine engine by determining whether the at least one thermal characteristic is indicative of a different operating parameter than the at least one operating parameter that is determined.

19. The system of claim 14, wherein the thermal remediation controller also is configured to determine a useful life, a remaining useful life, or a combination of the useful life and the remaining useful life of the turbine engine based on both the at least one operating parameter and the at least one thermal characteristic.

20. A method comprising:
  determining, by a controller, at least one operating parameter of a turbine engine that defines prior usage of the turbine engine, wherein the at least one operating parameter includes one or more of a prior performance characteristic of the turbine engine or a prior utilization characteristic of the turbine engine;

receiving, by the controller from one or more thermal sensors, an input indicative of a temperature of a first component of the turbine engine that engages a second component of the turbine engine during operation of the turbine engine;

determining at least one thermal characteristic of the turbine engine based at least in part on the received input, wherein the at least one thermal characteristic includes a thermal stress in at least one of the first component and the second component of the turbine engine caused at least in part by the first component engaging the second component due to thermal expansion;

determining, by the controller, whether both the at least one operating parameter and the at least one thermal characteristic indicate thermal degradation of the turbine engine; and implementing, by a remediation system, one or more remedial actions on the turbine engine to change a state of the turbine engine in response to determining, by the controller, that the at least one operating parameter and the at least one thermal characteristic indicate thermal degradation of the turbine engine.

21. The method of claim 20, wherein determining, by the controller, whether both the at least one operating parameter and the at least one thermal characteristic indicate the thermal degradation of the turbine engine involves determining, by the controller, whether the at least one thermal characteristic is indicative of a different operating parameter than the at least one operating parameter that is determined, wherein the at least one thermal characteristic is indicative of the different operating parameter when the at least one thermal characteristic is associated with more usage of the turbine engine than is indicated by the at least one operating parameter.

22. The method of claim 20, wherein determining the at least one thermal characteristic of the turbine engine comprises:

determining, by the controller, an amount of thermal expansion or contraction of the first component based at least in part on the input indicative of the temperature of the first component of the turbine engine that engages the second component of the turbine engine during operation of the turbine engine;

calculating, by the controller, an amount of stress imparted on at least one of the first component and the second component based at least in part on the amount of thermal expansion or contraction of the first component.

* * * * *